United States Patent [19]
Olson et al.

[11] Patent Number: 5,003,918
[45] Date of Patent: Apr. 2, 1991

[54] APPARATUS FOR MANUFACTURING ATHERECTOMY TORQUE TUBES

[75] Inventors: Thomas E. Olson, Poway; Dennis M. Vigil, San Diego, both of Calif.

[73] Assignee: InterVentional Technologies, Inc., San Diego, Calif.

[21] Appl. No.: 458,326

[22] Filed: Dec. 28, 1989

[51] Int. Cl.$^5$ ............................................. B05C 11/00
[52] U.S. Cl. ..................................... 118/665; 118/416; 156/356; 156/425; 156/546; 425/141
[58] Field of Search ................ 156/64, 356, 357, 425, 156/195, 446, 184, 185, 187, 188; 118/665, 404, 405, 416, 305, 320, 321; 427/9, 10; 425/135, 141

[56] References Cited

U.S. PATENT DOCUMENTS

| | | | |
|---|---|---|---|
| 2,269,032 | 1/1942 | Moore | 156/425 |
| 2,557,932 | 6/1951 | Baymiller | 156/425 X |
| 3,188,256 | 6/1965 | Shoemaker | 156/64 X |
| 3,231,442 | 1/1966 | Michael | 156/425 X |
| 3,612,058 | 10/1971 | Ackerman et al. | 128/348 |
| 3,618,614 | 11/1971 | Flynn | 128/348 |
| 3,731,671 | 5/1973 | Mageoh | 128/2.05 R |
| 3,789,841 | 2/1974 | Antoshkiw | 128/2.05 R |
| 3,811,449 | 5/1974 | Gravlee et al. | 128/343 |
| 3,968,800 | 7/1976 | Vilasi | 128/343 |
| 4,003,369 | 1/1977 | Heilman et al. | 128/2 M |
| 4,215,703 | 8/1980 | Wilson | 128/772 |
| 4,257,421 | 3/1981 | Beal | 128/348 |
| 4,287,223 | 9/1981 | Hackert et al. | 156/64 X |
| 4,362,163 | 12/1982 | Krick | 604/280 |
| 4,368,240 | 1/1983 | Nauta et al. | 118/321 X |
| 4,516,972 | 5/1985 | Samson | 604/282 |
| 4,572,186 | 2/1986 | Gould et al. | 128/341 |
| 4,653,496 | 3/1987 | Bundy et al. | 128/305 |
| 4,659,424 | 4/1987 | Baxter et al. | 156/64 X |
| 4,669,469 | 6/1987 | Gifford, III et al. | 128/305 |
| 4,679,557 | 7/1987 | Opie et al. | 128/305 |
| 4,696,667 | 9/1987 | Masch | 604/22 |
| 4,732,154 | 3/1988 | Shiber | 128/305 |

OTHER PUBLICATIONS

Jean Francois Fardeau, New Laser Sensors for Wire Diameter Measurement, Wire Journal International, Jan. 1989, pp. 43-50.

Primary Examiner—David A. Simmons
Attorney, Agent, or Firm—Nydegger & Associates

[57] ABSTRACT

An apparatus for manufacturing atherectomy torque tubes includes a mechanism for rotating a tube liner about its longitudinal axis at a rotational velocity. A carriage is translatably positioned along the longitudinal axis. A mechanism for winding a wire about the tube liner is mounted on the carriage. A mechanism for coating the tube liner with an epoxy material is also mounted on the carriage. In a preferred embodiment, wire is wound onto the tube liner inside a reservoir of urethane epoxy bath which is moved along the tube liner. A laser sensor measures the coated tube to provide a signal representative of the final outside diameter of the tube and a computer uses this signal to control the angular velocity of the rotating tube liner and the linear velocity of the carriage which moves the wire winding and coating mechanism along the tube. The computer also uses the signal to control a pressurized gas source which extrudes proper amounts of epoxy material out of the reservoir to coat the tube as the reservoir moves along the tube liner.

12 Claims, 3 Drawing Sheets

APPARATUS FOR MANUFACTURING ATHERECTOMY TORQUE TUBES

FIELD OF THE INVENTION

This invention relates generally to the manufacture of atherectomy cutter devices used to excise obstructions from blood vessels. More specifically, the invention relates to a system and apparatus for manufacturing a torque tube having a specified degree of torsional rigidity and stiffness for transmitting rotational torque from one end of the tube to the other end. The present invention is particularly, though not exclusively, useful for manufacturing torque tubes having one end attachable to a rotational drive mechanism, and the other end attachable to a rotatable atherectomy cutting head, in which the tube is able to bend and conform generally to the path of the blood vessel in which the excision is to occur.

BACKGROUND OF THE INVENTION

Removal of arterial obstructions formed by obstructive material in arteries and blood vessels has been made possible due to advances in medical treatment technology, and there are various methods currently employed. One such method involves introducing a flexible catheter into the cardiovascular system of a patient. The flexible catheter has a rotatable torque tube disposed in the lumen of the catheter, and the torque tube has a cutting apparatus attached to one end thereof for excising obstructive tissue from the artery. The flexible catheter and rotatable torque tube are introduced and steered along the blood vessel to the point of the obstruction. The rotary cutter can then be used to excise the obstructive tissue from the vessel. Specifically, the cutting apparatus has blades which are driven by the rotatable torque tube to excise obstructive tissue from the lumen of the blood vessel. To do this, the torque tube must be of sufficiently small size to fit into the artery of the patient and be able to be passed along the lumen of the vessel to the point of the obstruction. In addition, the torque tube must be flexible enough to accommodate the various bends and turns encountered in the vessel through which it must pass. The torque tube must be of sufficient stiffness, however, to be able to transmit torque from one end of the torque tube which is attached to the drive mechanism, to the other end of the torque tube which is attached to the cutting head. In addition, the torsional rigidity required must be firm enough to respond adequately to changes in the angular velocity of the drive mechanism so that the cutting head is responsive to changes in the rotational drive speed. Furthermore, in order to reduce the overall size of the cutting apparatus, it is desirable that the torque tube have a maximum inner diameter and minimum outer diameter, i.e. minimum acceptable wall thickness. It is also desirable that the torque tube be manufactured accurately within close tolerances.

Several methods have been proposed for manufacturing catheters for insertion into the cardiovascular system. They are not, however, necessarily utilized as torque tubes. For example, U.S. Pat. No. 4,516,972 to Samson discloses a guiding catheter and method of manufacture. A helically-wound ribbon of flexible material is embedded in the wall of the catheter to provide torsional rigidity and the stiffness of the catheter is controlled by varying the pitch of the helically-wound ribbon. In manufacturing the catheter, the catheter is covered with an outer jacket of flexible material fabricated of a thermal plastic material, such as polyethylene or heat-shrinkable tubing. In addition, the Samson patent discloses means for obtaining variations in torsional rigidity and stiffness by changing the pitch or density of the helical winding of the ribbon about the liner tube. The outer jacket comprises a length of heat-shrinkable tubing placed over the ribbon and heated to shrink fit. Unfortunately, there is no provision for monitoring or maintaining the accuracy of the outer diameter, nor for allowing appropriate adjustments to be made during its manufacture.

The present invention thus recognizes the need for a system for manufacturing torque tubes which provides desired flexibility and stiffness in various portions of the tube, yet maintains overall accuracy of the outside diameter. In addition, the present invention recognizes that rotating a liner tube at a specific angular velocity, in combination with the translational velocity of the wire being wound onto the liner tube, may determine the proper pitch and separation of the wire. In addition, the present invention recognizes that an outer layer may be applied onto the tube with required precision.

Accordingly, it is an object of the present invention to provide a method and apparatus for manufacture of torque tubes which provide desired torsional rigidity and flexibility to accommodate the needs of a particular patient undergoing an atherectomy procedure. It is a further object of the present invention to provide an apparatus and method for manufacturing a torque tube in which the outside diameter of the torque tube may be accurately maintained within desired tolerance limits. It is a further object of the present invention to provide a method and apparatus for manufacturing a torque tube which has minimal wall thickness and yet provides required flexibility and torsional rigidity for a given patient. It is yet another object of the present invention to provide a method and apparatus for manufacturing torque tubes in which the user may select various parameters for its construction, such as the pitch of the wire windings and the outside diameter, which parameters vary along the length of the tube to accommodate the path within a vessel. It is yet another object of the present invention to provide a method and apparatus for manufacturing torque tubes which is durable in construction and reliable and cost-effective in its manufacture and use. It is yet another object of the present invention to provide a method and apparatus for manufacturing torque tubes which is simple and convenient to use.

SUMMARY OF THE INVENTION

A preferred embodiment of the system and apparatus for manufacturing atherectomy torque tubes comprises a base having a mechanism for rotating a hollow tube liner about the longitudinal axis of the tube liner at a selected angular velocity. A carriage is mounted to the base and is translatable along the longitudinal axis of the tube liner and an apparatus for winding wire about the tube liner is mounted on the carriage. An advancing mechanism is mounted to the base for advancing the carriage and winding apparatus longitudinally along the tube liner axis. The advancing mechanism advances the winding apparatus along the tube liner at a selected linear velocity while, at the same time, the tube liner is rotated by the rotating mechanism to wrap the wire about the tube liner. By properly selecting the angular velocity of rotation for the tube liner, in combination with the linear velocity of the carriage, the wire is wrapped helically about the tube liner with a predetermined degree of pitch. In addition, a predetermined amount of separation between the respective wire wraps can be obtained. The mechanism for winding the wire around the tube liner includes a plurality of spools of wire to achieve the desired characteristics. The degree of pitch, in conjunction with the size of wire used and the material selected for the tube liner, determines the torsional rigidity and flexibility of the torque tube.

A coating mechanism for coating the wire wrapped tube liner is mounted on the carriage, which is advanced along with the wire winding apparatus. The coating mechanism coats the wrapped or wound tube with an outside layer of biocompatible material, such as urethane epoxy. The layer has an appropriate thickness to give the finished torque tube a desired outside diameter.

A computer is operatively coupled to the rotating mechanism, winding apparatus, the carriage advancing mechanism, and the coating mechanism. The computer stores a desired torque tube profile which is entered as input to the computer by the user. A feedback control system monitors the outside diameter of the torque tube and its angular velocity and linear velocity relative to the carriage, as it is being manufactured, and controllably adjusts these various parameters to achieve the desired torque tube profile. Specifically, a mechanism for monitoring the outside diameter of the wound and coated tube comprises a laser sensor assembly. This laser sensor assembly includes a laser diode, in cooperation with a collimator lens, to provide a collimated beam of light which is irradiated onto a charge coupled device. The laser sensor assembly is located so that the outside diameter of the coated tube is measured as it exits the manufacturing process to provide a constant monitoring of the outside diameter. The coated tube is positioned to provide a shadow onto the charge coupled device to generate a signal representative of the outside diameter of the coated tube. This signal is sent to the computer. With this signal and predetermined user input stored in the computer, which may include the wire size, liner tube size, desired pitch and wire separation, the computer controls the linear velocity of the advancing mechanism to adjustably maintain the outside diameter at the desired value. This is accomplished by comparing the measured diameter signal to the desired outside diameter value and generating an error signal indicating the amount of actual deviation from the desired value. The computer, which is responsive to the error signal, provides an angular velocity control signal to the winding apparatus to automatically adjust the angular velocity or speed of rotation of the tube. In addition, in response to the error signal, the computer provides a linear velocity control signal to the advancing apparatus to automatically adjust the linear velocity of the advancing apparatus. In this manner, the system maintains the predetermined pitch and wire separation. Also, the coating apparatus which is mounted on the advancing carriage, is thus responsive to changes in the linear velocity signal to further automatically adjust the thickness of the outside layer of coating to maintain the desired outside diameter value.

The coating mechanism in the preferred embodiment comprises a reservoir of liquid urethane bath which is contained in an enclosed container. The container has an entrance port and an exit port for the tube, and the tube is advanced through the container or pot through the ports. The urethane bath is subjected to pressure from a dry nitrogen atmosphere driven by a nitrogen pump. The amount of nitrogen pressure on the urethane bath controls the amount of urethane epoxy coating to be extruded from the exit port of the container over the wound tube as it emerges from the exit port of the container. The nitrogen pressure is controlled by the charge coupled device in combination with the computer. The amount of nitrogen pressure, in combination with the linear velocity of advancement of the reservoir along the tube, determines the thickness of the outside layer of coating deposited onto the wound tube, and thus the overall outside diameter of the finished torque tube.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
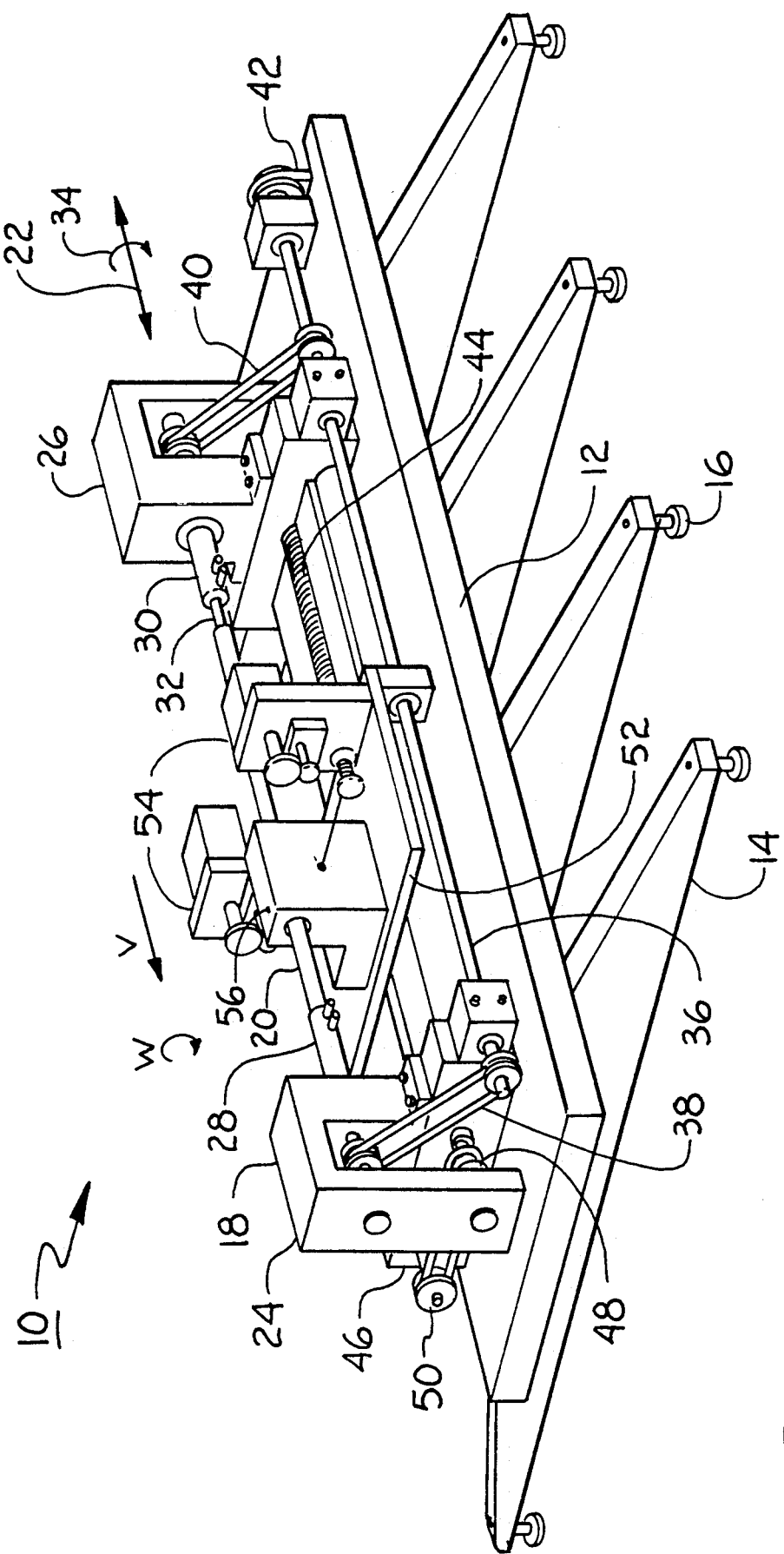
FIG. 1 is a perspective view of a preferred embodiment of the apparatus for manufacturing torque tubes in accordance with the present invention.

FIG. 1 shows an apparatus generally designated 10 for manufacturing atherectomy torque tubes in accordance with the present invention. Apparatus 10 comprises a base 12 having a plurality of legs 14 for supporting base 12. Legs 14 have leveling pads 16 for leveling base 12. In addition, leveling pads 16 help absorb shock for minimizing any unwanted vibration which may occur during operation of apparatus 10.

Mounted on base 12 is rotational drive assembly 18 for rotating a liner tube 20 about longitudinal axis 22. Liner tube 20 is a hollow tube liner made of a material compatible for use as a torque tube. A preferable material for tube 20 is a polyamide having an inside diameter suitable for performing atherectomy cutting procedures. Drive assembly 18 comprises a first drive assembly 24 and second drive assembly 26. First and second drive assemblies 24, 26 are driven by a common drive motor (not shown) for rotating the tube 20 at various angular velocities ω. The drive assemblies 24, 26 rotate a first drive assembly collet 28 and a second drive assembly collet 30, respectively. The first and second collets 28, 30 each support a mandrel 32 on which hollow tube 20 is rotatably carried. First drive assembly 24 and second drive assembly 26 are connected to a drive shaft 36 by drive belts 38, 40, respectively. Drive shaft 36 is rotatably driven by a drive belt 42 connected to a variable speed electric drive motor (not shown). Drive assembly 18 thus rotates tube 20 about axis 22 in a rotational direction, shown as clockwise arrow 34. In the preferred embodiment, it may be rotated at an angular velocity of approximately eight hundred (800) rotations per minute.

Mounted on base 12 is advancing screw 44 which is rotatably mounted parallel to longitudinal axis 22. Advancing screw 44 is rotationally driven by belt 46 having one end attached to screw end pulley 48 and another end attached to drive pulley 50. Drive pulley 50 is driven by a second variable speed electric motor (not shown). Advancing screw 44 is turned in a direction and at a rotational speed to advance the threads at a desired linear velocity v. The advancing screw 44 is coupled to a carriage plate 52 which moves the carriage plate 52 in translation generally along the longitudinal axis 22. Plate 52 is driven at linear velocity v in a forward or reverse direction depending upon the rotational direction of advancing screw 44 as driven by the drive pulley 50. Mounted on carriage plate 52 is wire source 54, which supplies the wire that is wound about liner tube 20. In addition, also mounted on carriage plate 52 is coating mechanism 56 for coating liner tube 20 with a layer of material to obtain a desired outside diameter thickness.

Figure 2:
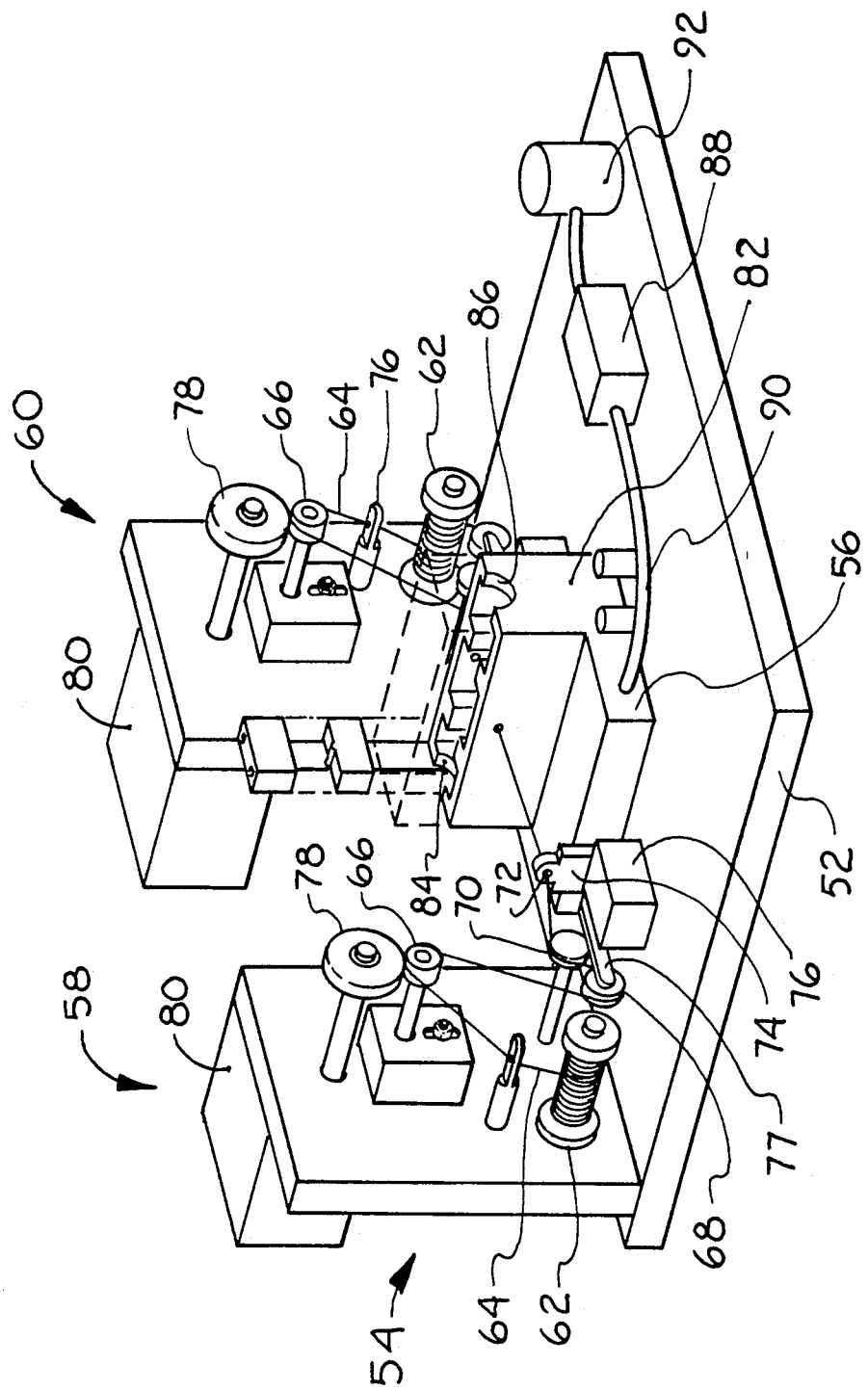
FIG. 2 is a perspective view of a carriage component of the apparatus shown in FIG. 1, partially exploded.

As can be best appreciated with reference to FIG. 2, there is shown the components of wire source 54 and coating mechanism 56 as mounted on carriage plate 52. In particular, there is shown in detail first portion 58 of wire source 54. The components of second portion 60, which correspond to the components of first portion 58, are as shown, substantially identical to that shown on first portion 58 of wire source 54 In particular, wire source 54 includes a spool for holding wire 64. Wire 64 is preferably a fine wire of high tensile strength, such as tungsten wire. The wire 64 is threaded over pulley 66, pulley 68, and pulley 70 as shown. After leaving pulley 70, wire 64 is threaded through eye 72 of wire block 74. First portion 58 also includes a sensor 76 which is connected to pulley 68 via lever 77. As so positioned, sensor 76 monitors the tension of wire 64 between pulley 66 and drive wheel 78 driven by an electric motor (not shown) housed inside casing 80.

A coating mechanism 56 is mounted on carriage plate 52. It is shown in FIG. 2 in a partially exploded view. In particular, coating mechanism 56 includes a reservoir 82 for containing a bath of urethane epoxy. Further, reservoir 82 includes an entrance port 84 and an exit port 86 of sufficient size to allow passage of liner tube 20 wrapped with wire 64 to be passed therethrough. Reservoir 82 is connected to a dry nitrogen atmosphere pressure source 92 and nitrogen pump 88 by tube 90. As intended for apparatus 10, pump 88 controls the pressure of nitrogen gas fed by gas source 92 into reservoir 82 which, in turn, controls the speed with which urethane epoxy contained in reservoir 82 is extruded from exit port 86 about liner tube 20.

Figure 3:
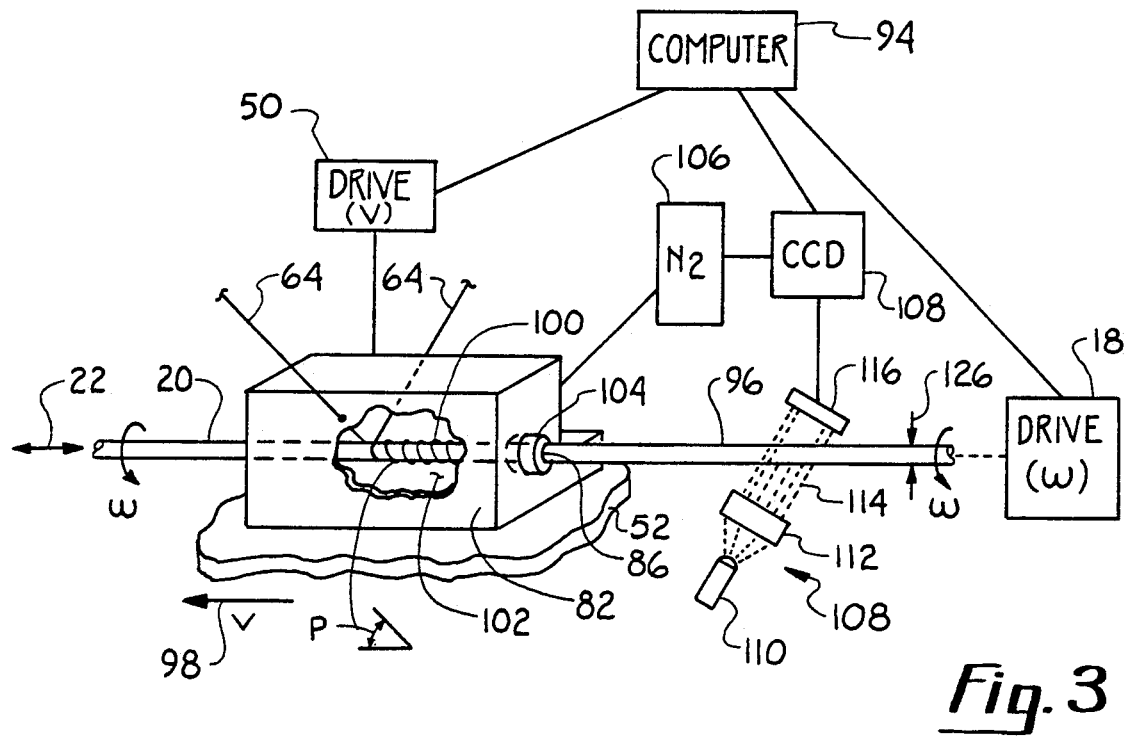
FIG. 3 is a block flow diagram of a control system for use in practicing the preferred embodiment of the present invention.

Referring now to FIG. 3, there is shown the operation of the system. In particular, liner tube 20 is rotated about longitudinal axis 22, by rotational drive assembly 18 with an angular velocity $\omega$ which is controlled by a computer 94. A preselected size of liner tube 20 is selected by the user as having a desired inside and outside diameter to yield a final outside diameter of finished torque tube 96. In addition, a desired thickness of wire 64 is chosen for the appropriate torque tube thickness and strength characteristics. With respect to reservoir 82, various size reservoirs 82 can be used with variable sized exit ports 86 to determine the overall final outside diameter of finished torque tube 96. In addition, the user may specify the desired pitch, or angle, p, of the wire 64 being wound about liner tube 20 inside reservoir 82. As will be appreciated by the skilled artisan, pitch p is controlled by the combined effects of the linear velocity v of carriage plate 52, which carries wire sources 56, and the angular velocity $\omega$ of tube 20. Further, the speed with which carriage plate 52 advances generally in the direction of arrow 98 with velocity v along axis 22, in combination with angular velocity $\omega$, determines also the separation of wires 64 about portion 100 of liner tube 20. It has been found that the flexibility of tube 20 varies with the angle of pitch p of wire 64 wound around tube 20. For example, forty-five degrees (45°) generates a winding pitch which maximizes transmission of torque, but does not necessarily yield the most flexibility.

Drive pulley 50 which controls the magnitude of linear velocity v is controlled by computer 94 which is coupled to drive pulley 50. Wound portion 100 of liner tube 20, in addition to being wound at the desired pitch p, is wound inside reservoir 82. Wound portion 100 is thus enveloped in liquid urethane bath material 102 carried inside reservoir 82. As reservoir 82 is moved along liner tube 20 generally in the direction of arrow 98, extruded urethane epoxy 104 exits from exit port 86. Epoxy 104 forms a coating on wound portion 100 of liner tube 20 to cover torque tube 96 with a layer of coating of a desired thickness. The thickness of extruded layer 104 is, in part, a function of the speed with which reservoir 82 is moved along tube 20 by carrige 52. If carriage 52 is moving at a higher speed, extruded layer 104 is spread thinner onto torque tube 96. The thickness of extruded layer 104 is also a function of the pressure with which liquid epoxy 102 is forced from within reservoir 82. This pressure is generated by pressurized gas source 106 which is varied by a laser sensor 108. In addition, the size of exit port 86 with respect to the outside diameter of liner tube 90, in combination with the speed of carriage 52 and the pressure inside reservoir 82 established by pressurized gas source 106, are also factors which control the final outside diameter thickness of torque tube 96.

Figure 4:
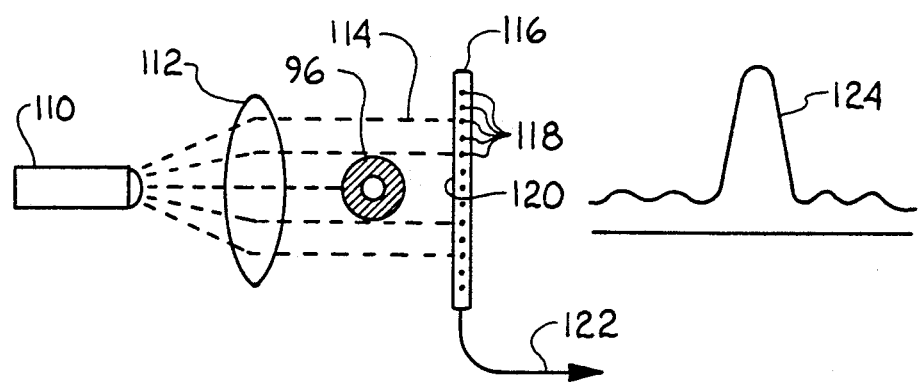
FIG. 4 is a schematic illustration of a laser sensor system for measuring the outside diameter of the tube in accordance with the present invention.

A feedback loop mechanism is used to maintain the desired outside diameter thickness of torque tube 96 and includes a laser sensor apparatus generally indicated 108 in FIG. 3. In particular, the laser sensor 108 can be used to measure outside diameter of torque tube 96 with the extruded coating or layer 104 thereon. More particularly, laser sensor apparatus 108 comprises laser light source 110 which generates a laser beam that is passed through a lens 112 which directs a collimated beam 114 of laser light at a charge coupled device 116. The shadow generated by torque tube 96 positioned between lens 112 and sensor 116 provides an indicator of the outside diameter thickness of torque tube 96. This can perhaps best be appreciated with reference to FIG. 4 in which the components of the laser sensor apparatus are shown. As indicated in FIG. 4, charge coupled device 116 includes a number of pixels 118. For the purpose of measuring the outside diameter of the torque tube 96, the portion of the pixels 118 in the shadow of torque tube 96 generates a signal 122. Specifically, signal 122 is representative of the light output signal wave form 124, and, as is well known, the shape of this wave form 124 can be read to accurately determine the outside diameter of torque tube 96. This information is sent from charge coupled device 16 and input to the computer 94.

With continuous information of the thickness of torque tube 96, computer 94 thus controls the linear velocity, angular velocity, and pressure of reservoir 82 to maintain and adjustably control the thickness of torque tube 96 as it is produced by the above-mentioned manufacturing process. Conversely, should the thickness of torque tube 96 become less than desired, the pressure of pressurized gas source 106 can be increased to increase the thickness of extruded layer 104. Additionally, the linear velocity v of carriage plate 52 can be slowed so that more liquid epoxy is extruded from exit port 86. However, slowing of linear velocity v also effects pitch p. In order to maintain the desired pitch p in wound portion 100 of tube 20, the angular velocity $\omega$ is appropriately slowed down by drive 18, also controlled by computer 94. Thus, the desired pitch is maintained as is the desired final outside diameter thickness of torque tube 96.

Moreover, with respect to the computer 94, various lengths of torque tube 96 can be programmed so that there is varying pitch and wire separation at various portions of the tube. This allows manufacture of a torque tube which fits the profile of the blood vessel into which it is to be inserted. The rotational drive 18 and angular velocity $\omega$, as well as the linear velocity drive 50 and linear velocity v can be adjustably changed to generate the desired pitch p. Also, the pressure of pressurized gas source 106 can be adjustably varied to maintain the desired extruded layer 104 thickness as indicated by the laser sensor apparatus 108. Thus, the present invention allows change in flexibility and strength of the tube in order to accommodate the needs of a specific patient. Moreover, it can be seen that even the outside diameter of the torque tube 96 can be adjusted. However, it is more easily adjusted by selecting the proper liner tube 20 diameter and sizes, as well as the appropriate size and type of wire 64 to also allow the desired final torque tube 96 to be manufactured.

While the particular apparatus for manufacturing atherectomy torque tubes as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

What is claimed is:

1. An apparatus for manufacturing atherectomy torque tubes, comprising:
   means for winding a wire around a tube liner with a selected pitch and wire separation to provide a wound tube;
   means for applying a coating onto said wound tube at a rate which generates a thickness of material to establish an outside diameter for said tube;
   means for providing a signal representing a desired outside diameter;
   means for measuring said outside diameter of said coated tube and generating a signal representative of an amount of deviation of said measured diameter from said desired diameter; and
   control means coupled to said coating means and said winding means for varying said rate of application of said coating to attenuate said deviation signal, while maintaining said selected pitch and wire separation on said tube.

2. An apparatus for manufacturing atherectomy torque tubes as recited in claim 1, wherein said means for winding comprises a wire feed source, means for rotating said tube liner about its longitudinal axis at an angular velocity, and means for advancing said wire feed source along said tube liner at a linear velocity to wind said wire around said tube liner at said selected pitch and wire separation.

3. An apparatus for manufacturing atherectomy torque tubes as recited in claim 2, wherein said coating means comprises a container of coating material mounted adjacent said wire feed source and advanced along said tube at said linear velocity.

4. An apparatus for manufacturing atherectomy torque tubes as recited in claim 3, wherein said measuring means includes a laser sensor.

5. An apparatus for manufacturing atherectomy torque tubes as recited in claim 4, further comprising means for storing a desired winding profile for said tube including defined portions of said tube, each portion having selected pitch and wire separation.

6. An apparatus for manufacturing atherectomy torque tubes as recited in claim 1, wherein said coating means comprises a bath of coating material through which said wound tube is passed.

7. An apparatus for manufacturing atherectomy torque tubes as recited in claim 6, further comprising a container for holding said bath, said container having an entrance port and an exit port for said tube, and a pressure source connected to said container for extruding said coating material out from said exit port to coat said tube.

8. An apparatus for manufacturing atherectomy torque tubes as recited in claim 7, further comprising means for controlling said pressure source to vary the amount of coating material extruded from said outlet over said tube.

9. An apparatus for manufacturing atherectomy torque tubes as recited in claim 8, further comprising means for advancing said container along said tube for varying the thickness of extruded coating material coating said tube.

10. An apparatus for manufacturing atherectomy torque tubes as recited in claim 9, wherein said means for controlling said pressure includes a charge coupled device.

11. An apparatus for manufacturing atherectomy torque tubes, comprising:
    means for rotating a hollow tube liner about its longitudinal axis at a selected angular velocity;
    means for winding a wire about said tube liner;
    means for coating said wire wound tube liner with an outside layer having a thickness, said wrapped and coated tube having an outside diameter;
    means for advancing said winding means and said coating means longitudinally along said axis at a selected linear velocity to wrap said wire about said tube liner at a predetermined degree of pitch;
    means for storing a desired outside diameter value;
    means for measuring said outside diameter of said wound and coated tube and providing a signal indicative of said measured outside diameter;
    comparing means for comparing said measurement diameter signal to said desired value and generating a signal indicating a deviation from said desired value;
    feedback control means coupled to said comparing means responsive to said deviation signal for providing an angular velocity control signal to said rotating means to automatically adjust said angular velocity and for providing a linear velocity control signal to said advancing means to automatically adjust said linear velocity of said advancing means to attenuate said deviation to maintain said predetermined pitch.

12. An apparatus for manufacturing atherectomy torque tubes as recited in claim 11, wherein said feedback control means is carried in said advancing means and is responsive to said linear velocity signal to automatically adjust said thickness of said outside layer to maintain said desired outside diameter value.

* * * * *